(12) United States Patent
Anderson, Jr. et al.

(10) Patent No.: US 7,288,176 B2
(45) Date of Patent: Oct. 30, 2007

(54) METHOD AND APPARATUS FOR GENERATING HIGH PURITY ELUANT

(75) Inventors: James M. Anderson, Jr., Arlington Heights, IL (US); Raaidah Saari-Nordhaus, Antioch, IL (US)

(73) Assignee: Dionex Corporation, Sunnyvale, CA (US)

( * ) Notice: Subject to any disclaimer, the term of this patent is extended or adjusted under 35 U.S.C. 154(b) by 736 days.

(21) Appl. No.: 10/421,608

(22) Filed: Apr. 23, 2003

(65) Prior Publication Data

US 2004/0214344 A1   Oct. 28, 2004

(51) Int. Cl.
 *B01D 61/42* (2006.01)
(52) U.S. Cl. ..................... 204/551; 204/647
(58) Field of Classification Search ........... 204/551, 204/647
See application file for complete search history.

(56) References Cited

U.S. PATENT DOCUMENTS

| | | | |
|---|---|---|---|
| 4,636,296 A | 1/1987 | Kunz | |
| 4,687,561 A | 8/1987 | Kunz | |
| 4,806,236 A | 2/1989 | McCormack | |
| 4,847,598 A | 7/1989 | Tucci et al. | |
| 4,880,513 A | 11/1989 | Davis et al. | |
| 5,045,204 A | 9/1991 | Dasgupta et al. | |
| 5,173,164 A | 12/1992 | Egen et al. | |
| 5,336,387 A | 8/1994 | Egen et al. | |
| 5,352,345 A | 10/1994 | Byszewski et al. | |
| 5,451,309 A | 9/1995 | Bell | |
| 5,518,622 A | 5/1996 | Stillian | |
| 5,567,307 A | 10/1996 | Karmarkar | |
| 5,597,481 A | 1/1997 | Stillian et al. | |
| 5,759,405 A | 6/1998 | Anderson, Jr. et al. | |
| 5,773,615 A | 6/1998 | Small et al. | |
| 5,914,025 A | 6/1999 | Small | |
| 5,935,443 A | 8/1999 | Anderson, Jr. | |
| 6,027,643 A | 2/2000 | Small et al. | |
| 6,036,921 A | 3/2000 | Small et al. | |
| 6,093,327 A * | 7/2000 | Anderson et al. | 210/660 |
| 6,225,129 B1 | 5/2001 | Liu et al. | |
| 6,235,197 B1 | 5/2001 | Anderson, Jr. | |
| 6,315,954 B1 | 11/2001 | Small et al. | |
| 6,316,270 B1 | 11/2001 | Small et al. | |
| 6,316,271 B1 | 11/2001 | Small et al. | |
| 6,325,976 B1 | 12/2001 | Small et al. | |
| 6,334,941 B1 | 1/2002 | Iwamoto | |
| 6,338,784 B1 | 1/2002 | Terada et al. | |
| 6,444,475 B1 | 9/2002 | Anderson, Jr. | |
| 6,468,804 B1 | 10/2002 | Anderson, Jr. et al. | |
| 6,495,371 B2 | 12/2002 | Small et al. | |

(Continued)

FOREIGN PATENT DOCUMENTS

FR   2659869   9/1991

*Primary Examiner*—Arun S. Phasge
(74) *Attorney, Agent, or Firm*—David J. Brezner; Morgan, Lewis & Bockius LLP

(57) ABSTRACT

A method and apparatus is provided for generating a high purity eluant suitable for use in chromatography. The high purity eluant may be generated by providing water and a first stationary phase comprising exchangeable cations. Electrolysis ions are generated by the electrolysis of water. The electrolysis ions are selected from the group consisting of hydronium ions and hydroxide ions. The hydronium ions are passed through the first stationary phase so that the hydronium ions replace the cations in the first stationary phase. Thereafter, a source of desired ions is combined with the cations to form a high purity eluant containing the desired ions.

22 Claims, 4 Drawing Sheets

U.S. PATENT DOCUMENTS

| | | |
|---|---|---|
| 6,508,985 B2 | 1/2003 | Small et al. |
| 6,558,551 B1 | 5/2003 | Anderson, Jr. |
| 6,610,546 B1 | 8/2003 | Liu et al. |
| 6,613,235 B1 * | 9/2003 | Anderson et al. ........... 210/670 |
| 6,682,701 B1 | 1/2004 | Liu et al. |
| 6,709,583 B2 | 3/2004 | Anderson, Jr. et al. |
| 2001/0019031 A1 | 9/2001 | Anderson, Jr. |
| 2001/0026773 A1 | 10/2001 | Small et al. |
| 2001/0026774 A1 | 10/2001 | Small et al. |
| 2002/0177233 A1 | 11/2002 | Liu et al. |
| 2002/0182741 A1 | 12/2002 | Liu et al. |
| 2002/0192832 A1 | 12/2002 | Anderson, Jr. |
| 2003/0209439 A1 | 11/2003 | Anderson, Jr. |
| 2003/0209494 A1 | 11/2003 | Anderson, Jr. |

* cited by examiner

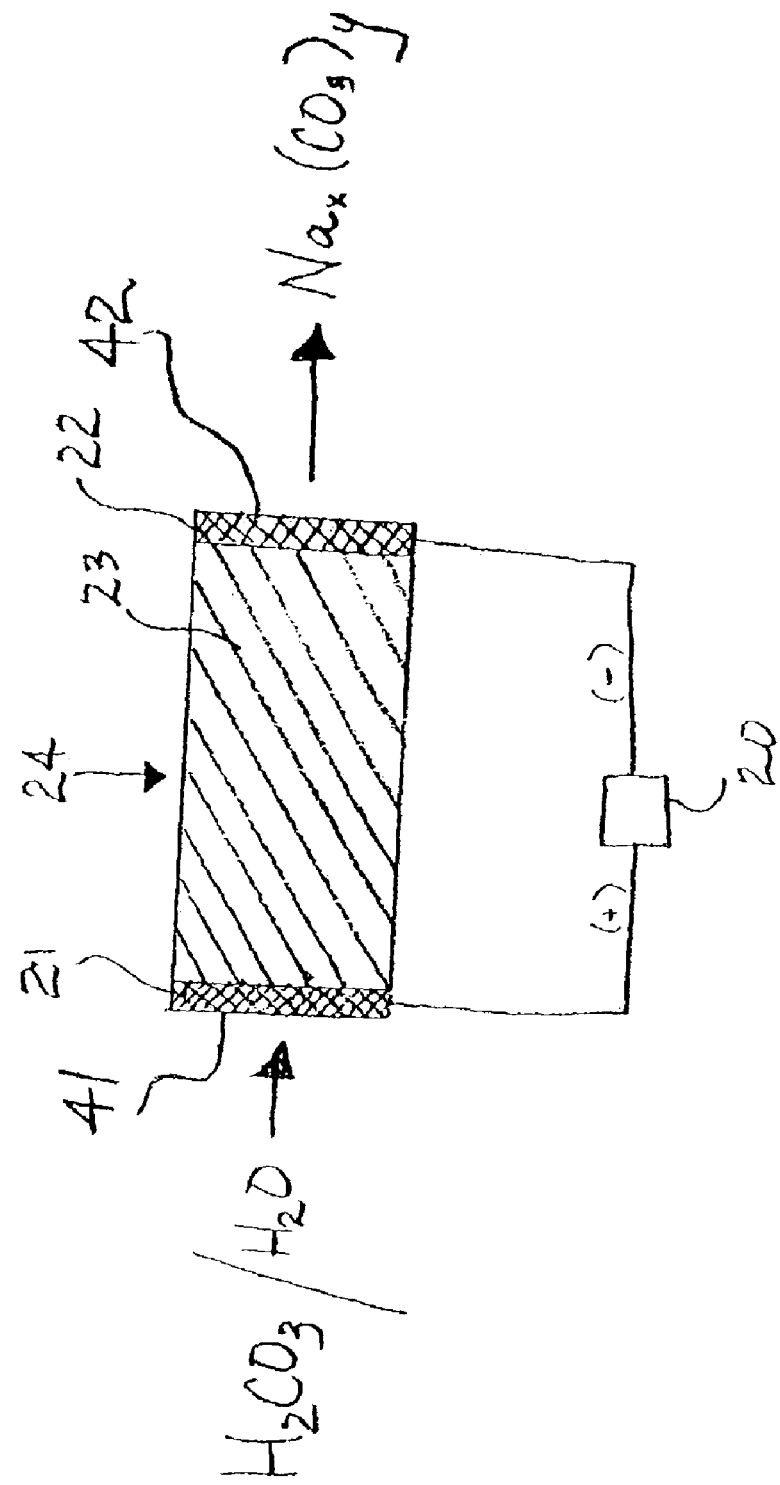

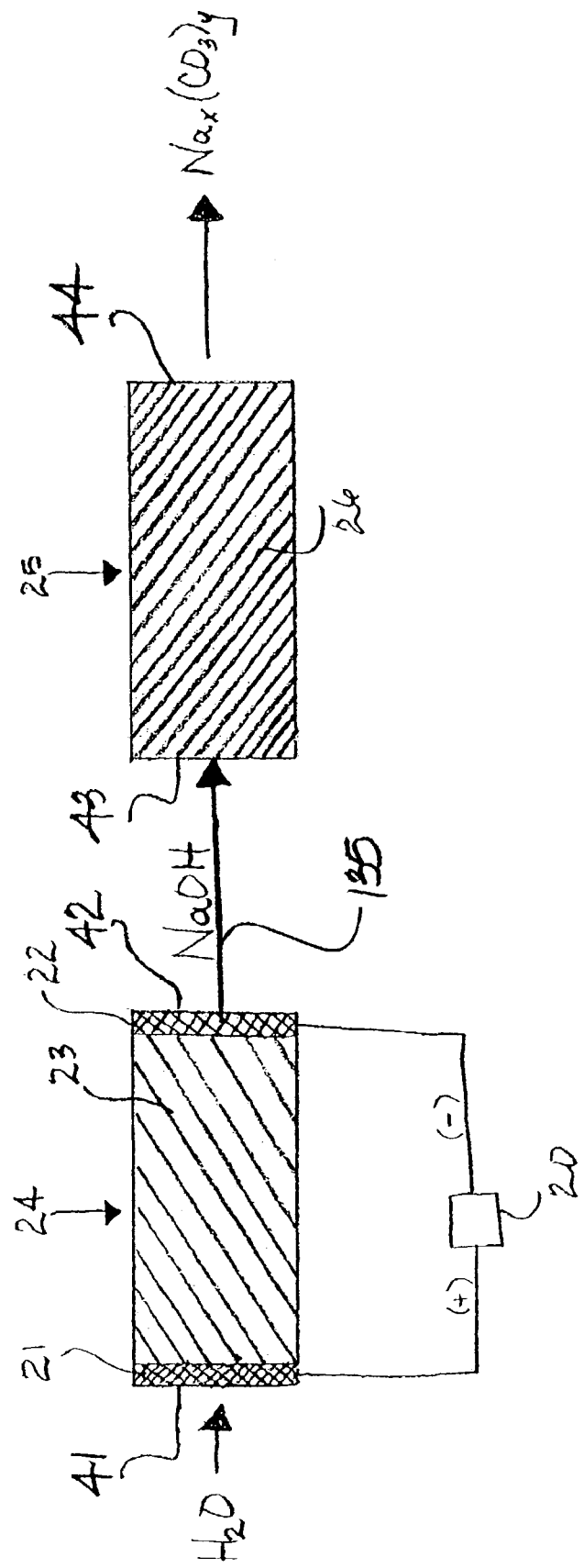

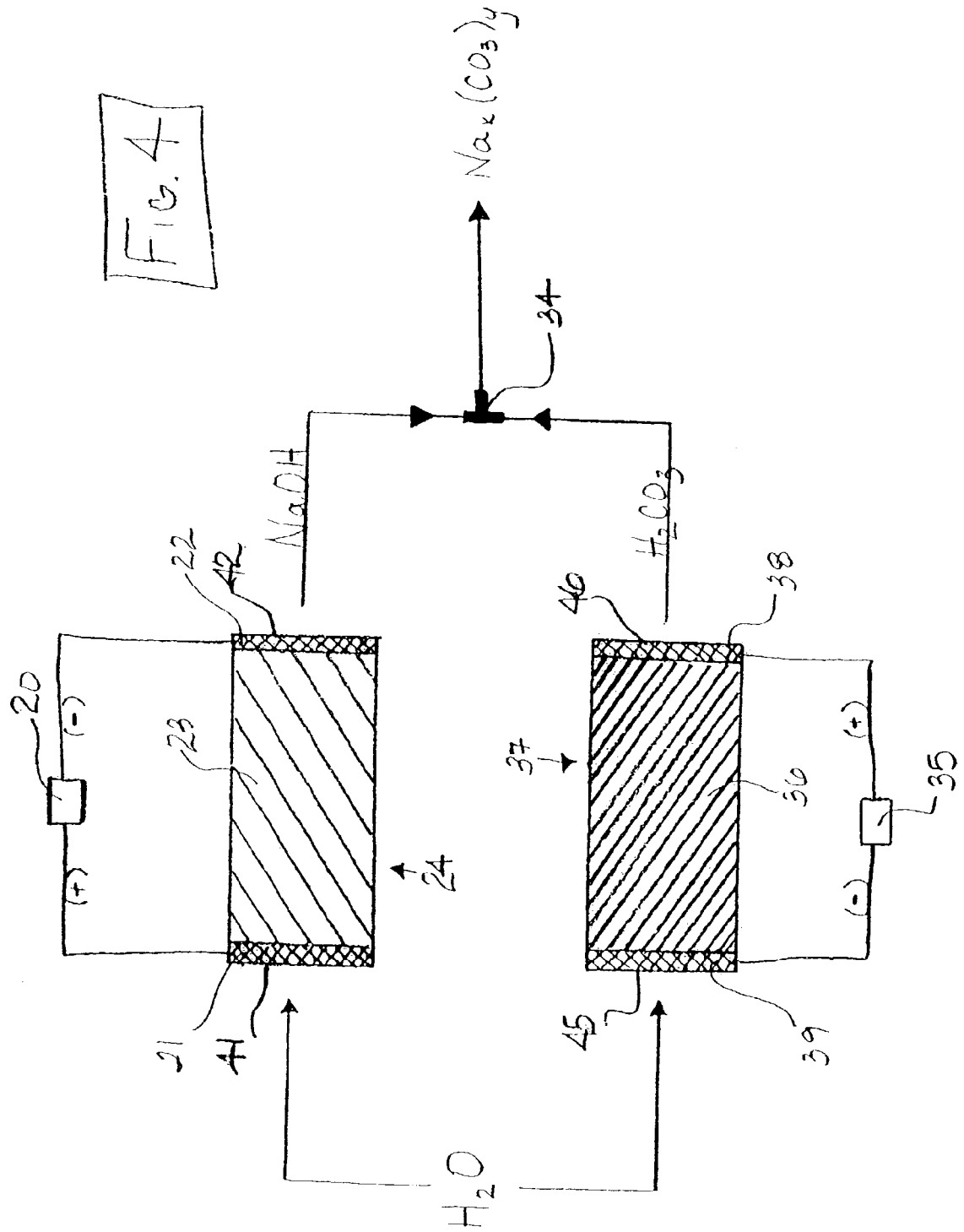

METHOD AND APPARATUS FOR GENERATING HIGH PURITY ELUANT

This invention relates to a method and apparatus for the generation of a high purity eluant suitable, for example, for ion chromatography.

One effective form of liquid chromatography is referred to as ion chromatography. In this known technique, the ions in a sample solution are typically directed through a chromatographic separation stage using an eluant containing an electrolyte. Thereafter, the eluant/sample solution is routed to a suppression stage, followed by detection, typically by an electrical conductivity detector. In the suppression stage, the electrical conductivity of the eluant is suppressed but not that of the separated ions so that the latter may be detected by a conductivity cell. This technique is described in detail, for example, in U.S. Pat. Nos. 3,897,213, 3,920,397, and 3,925,019.

There is a general need for high purity eluants for liquid chromatography and a particular need in ion chromatography. Similarly, there is a need for a convenient way to generate gradient eluants of precise concentrations and timing. There is also a need to generate gradient eluants, which are eluants having different strengths and concentrations that are used during the course of a single chromatography run. The use of gradient eluants for ion chromatography is described in Rocklin, R. D., et al. J. of Chromatographic Science, Vol. 27, p. 474, August 1988; Qi, D., et al. Analytical Chemistry, Vol. 61, p.1383, 1989; and Shintani, H., et al., Analytical Chemistry, Vol. 59, p. 802, 1987.

A method and apparatus for generating a high purity sodium hydroxide solution for use as a chromatography eluant is described in U.S. Pat. No. 5,759,405. A method and apparatus for generating a high purity potassium hydroxide solution for use as a chromatography eluant is described in U.S. Pat. No. 6,036,921. These patents, however, do not describe a method or apparatus for generating a high purity eluant comprising carbonate ions. A highly pure eluant comprising carbonate ions is especially useful in the isocratic separation of divalent or trivalent anions. In such applications, moreover, the concentration of carbonate ions required is significantly less than that required with other eluants such as sodium hydroxide or potassium hydroxide.

SUMMARY OF THE INVENTION

In accordance with the present invention, a method and apparatus is provided for generating a high purity carbonate eluant suitable for use in chromatography. The high purity eluant may be generated by providing water and a first stationary phase comprising exchangeable cations. Electrolysis ions are generated by the electrolysis of water. The electrolysis ions are selected from the group consisting of hydronium ions and hydroxide ions. The hydronium ions are passed through the first stationary phase so that the hydronium ions replace the cations in the first stationary phase. Thereafter, carbonate ions from a source of carbonate ions are combined with the cations to form a high purity eluant containing carbonate ions.

Another aspect of the present invention provides a high purity eluant by providing water and providing a first stationary phase comprising exchangeable cations. Electrolysis ions are generated by the electrolysis of water. The electrolysis ions are selected from the group consisting of hydronium ions and hydroxide ions. The hydronium ions are contacted and exchanged with the cations in the first stationary phase to form a cation hydroxide solution. Desirably, the cation is sodium. A second stationary phase comprising exchangeable carbonate ions is provided. The hydroxide ions from the cation hydroxide solution are contacted and exchanged with the carbonate ions in the second stationary phase so that the hydroxide ions replace the carbonate ions in the second stationary phase and a cation carbonate solution is formed.

In another aspect of the present invention, the high purity eluant is generated by providing water and providing a first stationary phase comprising cations. A second stationary phase comprising carbonate ions is also provided. Electrolysis ions are generated in each of the first and second stationary phases by the electrolysis of water wherein the electrolysis ions are selected from the group consisting of hydronium ions and hydroxide ions. The hydronium ions are exchangeable with the cations in the first stationary phase and the hydroxide ions are exchangeable with the carbonate ions in the second stationary phase. The hydronium ions are passed through the first stationary phase so that the hydronium ions replace the cations in the first stationary phase to form a cation hydroxide solution. The cation may be selected from the group consisting of sodium, potassium, and lithium. The hydroxide ions are passed through the second stationary phase so that the hydroxide ions replace the carbonate ions in the second stationary phase to form a carbonic acid solution. The cation hydroxide solution is combined with the carbonic acid solution to form a cation carbonate solution.

BRIEF DESCRIPTION OF THE DRAWINGS

FIG. 2 is a schematic view of an embodiment of an apparatus according to the present invention for generating a high purity eluant.

FIG. 3 is a schematic view of another embodiment of an apparatus according to the present invention for generating a high purity eluant.

FIG. 4 is a schematic view of a further embodiment of an apparatus according to the present invention for generating a high purity eluant.

DESCRIPTION

Figure 1:
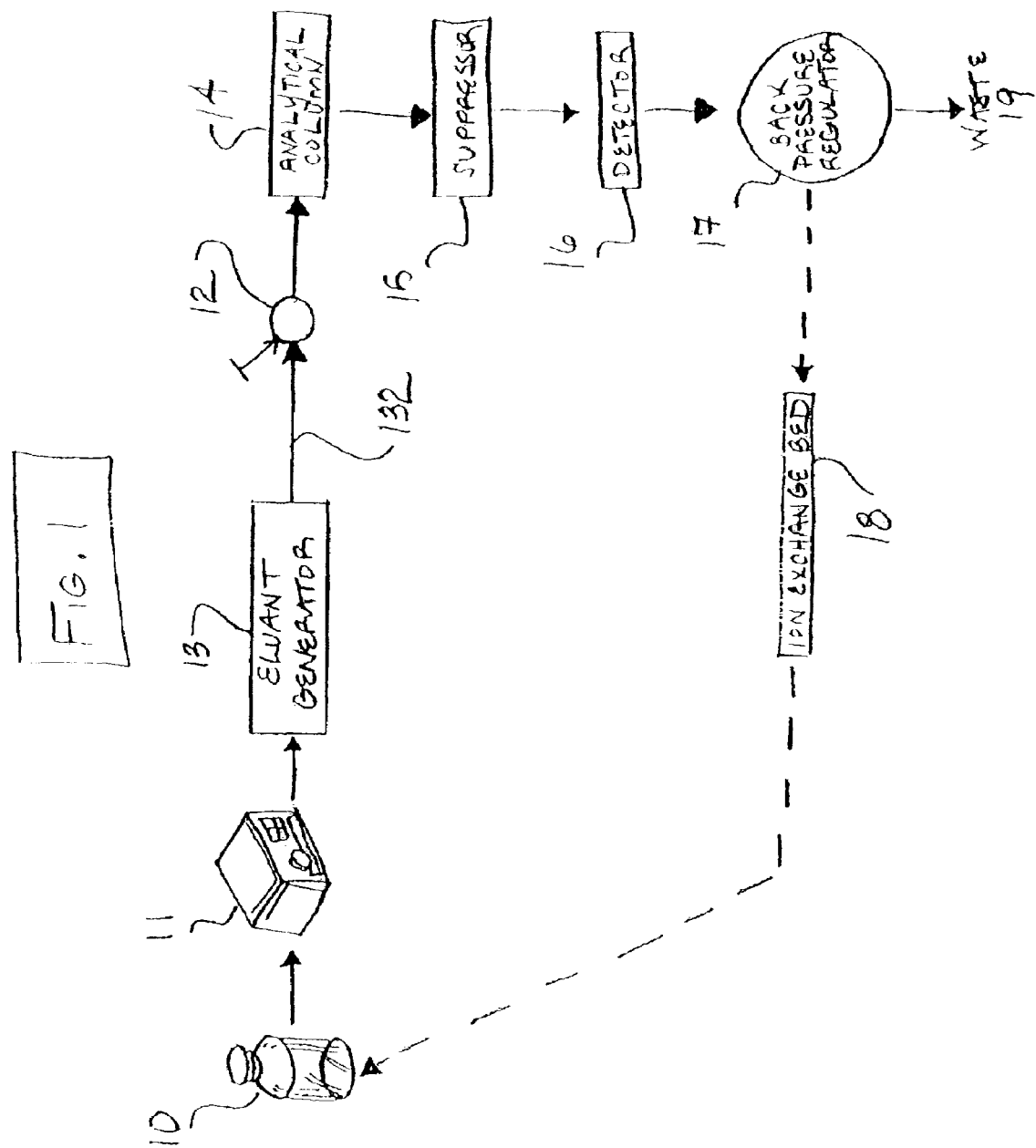
FIG. 1 is a schematic view of an ion chromatography apparatus.

Turning to FIG. 1, a simplified ion chromatography apparatus is illustrated. The apparatus includes a source of an aqueous stream such as a deionized water reservoir 10. The aqueous stream (containing deionized water) is pumped by a pump 11 through an eluant generator 13 that generates an eluant as described below. The effluent of the eluant generator 13 desirably travels through a gas permeable tubing or membrane 132 to a sample injection valve 12. The gas permeable tubing 132 is any suitable tubing that will contain liquids yet allow gas to pass through the tubing to reduce or eliminate gas present with or in the liquid. A suitable tubing is TEFLON AF 2400 (DUPONT) available from BIOGENERAL of San Diego, Calif., or TEFLON AF available from SYSTEC INC. of New Brighton, Minn. By flowing the eluant generator effluent through the tubing 132, gas that is produced during the generation of eluant can be removed from the system prior to sample introduction.

The eluant generator effluent is combined with the liquid sample containing the sample ions and the mixture is routed through an analytical column 14 where the sample ions are separated. The analytical column 14 may be in fluid communication with a suppressor column 15 which serves to suppress the conductivity of the eluant but not the sample ions. The effluent from the suppressor column 15 is routed to a detector 16 in which the sample ions are detected. Alternatively, the effluent of the analytical column 14 may be directed directly to the detector 16.

The detector effluent is then routed through a back pressure regulator 17 to waste 19. Alternatively, the detector effluent may be routed through the back pressure regulator 17 and then through an ion exchange bed 18 to be recycled to the water reservoir 10.

The back pressure regulator 17 may aid in forcing the gases generated in the eluant generator 13 through the gas permeable tubing 132. The back pressure regulator 17, however, is not necessary when the gas permeable tubing 132 is used. Thus, as a further alternative, the detector effluent may be routed directly to waste 19 and/or through the ion exchange bed 18 to be recycled to the water reservoir 10.

With the exception of the eluant generator 13, ion chromatography apparatuses such as that illustrated in FIG. 1 are well known by those skilled in the art. For example, such apparatuses are described in U.S. Pat. No. 5,759,405, the entire disclosure of which is incorporated herein by reference.

FIG. 2 illustrates an embodiment of the eluant generator 13 of the present invention, which comprises a column 24. The column 24 is typically in the form of a hollow cylinder, but it may be constructed in accordance with any of the procedures and column apparatuses known in the art, such as that disclosed in U.S. Pat. No. 5,759,405.

The column 24 comprises a stationary phase 23 disposed within the column 24. The stationary phase 23 may include a cation exchange packing material with exchangeable cations. Non-limiting examples of exchangeable cations are those selected from the group consisting of sodium, potassium, and lithium ions. For ease of reference, the figures and description refers to the exchangeable cations as sodium. It is to be understood that, unless expressly stated otherwise, when reference is made to sodium, it also encompasses other exchangeable cations.

Suitable cation exchange packing materials include acid functionalized organic and inorganic particles, such as phosphoric acid functionalized organic or inorganic particles, carboxylic acid functionalized organic or inorganic particles, sulfonic acid functionalized organic or inorganic particles, and phenolic acid functionalized organic or inorganic particles. Desirable cation exchange packing materials are sulfonic acid functionalized particles.

The cation exchange packing materials may be packed into the column 24, for example, in resin form, impregnated into a membrane, or in the form of a monolith (porous rod) material. In one embodiment, the cation exchange packing material is packed in the column 24 in resin form. In view of the foregoing, those skilled in the art will appreciate the term "stationary phase" as used in the specification and claims is meant to include, for example, chromatography packing material, coatings of chromatography material containing chromatography stationary phases coated on the wall proximate to the flow of the aqueous stream, hollow tubing containing chromatography stationary phases, as well as other stationary phases commonly used in chromatography.

The column 24 further comprises electrodes 21 and 22 at an upstream end 41 and downstream end 42 of column 24, respectively. The electrodes 21 and 22 are positioned at opposite ends of the column 24, and are positioned such that the flow of aqueous stream through the stationary phase 23 is from the electrode 21 at the upstream end 41 to the electrode 22 at the downstream end 42.

In one embodiment, the electrode 21 is the anode and the electrode 22 is the cathode. The electrodes 21 and 22 are generally flow-through electrodes. By flow-through electrodes, it is meant that the electrodes allow the sample ions, water, and/or eluant to flow through them.

The electrodes can be made from carbon, platinum, titanium, stainless steel or any other suitable conductive, non-rusting material. Desirably, the electrodes are made of platinum coated titanium, ruthenium oxide coated titanium, titanium nitride coated titanium, gold, or rhodium with an average pore size of between 0.1 μm and 100 μm. The flow-through electrodes are sufficiently porous to allow the sample ions, water, and eluant to flow through the electrodes, but are sufficiently non-porous to physically retain the stationary phase 23 disposed in the column 24.

The electrodes can be located either outside of or inside the column 24. The only necessary condition with respect to the placement of the electrodes is that at least a portion of the stationary phase 23 is disposed between the two electrodes 21 and 22, and that flow of the aqueous stream through the column 24 is in a direction from one of the electrodes toward the other electrode. Thus, when it is said that the electrode is positioned at an "upstream end" of the column, it does not necessarily mean that the electrode is actually located in the column. To the contrary, it is simply meant that the electrode is located on the side of the column 24 toward the aqueous stream source (water reservoir 10) relative to the other electrode. Similarly, by the term "downstream end" of the column, it is meant that the electrode is located on the side opposite the aqueous stream source (water reservoir 10) relative to the other electrode. Again, the electrode is not necessarily positioned in the column itself. In other words, the electrodes may be physically located with respect to the stationary phase such that the electrodes are adjacent the respective inlet and outlet of the column 24.

The electrodes 21 and 22 are connected to an electrical power source 20. As those skilled in the art will appreciate, a variety of electrical power supplies may suitably be used in the present invention. All that is required for the electrical power supply is that it be capable of providing sufficient voltage to the electrodes for the electrolysis of the water flowing in the aqueous stream to occur. A time-programmable constant current DC power supply is desirable, such as the LABCONCO Model 3000 Electrophoresis Power Supply.

When the power source 20 is energized, an electric current, caused by ion transport, is established between the electrodes 21 and 22 and across the stationary phase 23 when the column 24 is in use. The electric current follows along a path that is parallel to the flow of the aqueous stream through the column 24. Desirably, the current is a constant current.

The strength of the current generated in column 24 is directly proportional to the voltage applied at the electrodes, the cross-section area of the electrodes, and the capacity of the stationary phase 23 in column 24 (e.g. the higher the capacity of the stationary phase 23, the lower the resistance is in the column 24). Furthermore, the strength of the current in column 24 is inversely related to the distance between the two electrodes.

Without being restricted to any particular theory, it is presently believed that the electrical current in column 24 is generated between the two electrodes 21 and 22 via ion transport along the stationary phase 23 in the column 24.

Where the stationary phase 23 is not capable of ion transport, however, it is presently believed that ion transport takes place via the mobile phase.

With reference to FIG. 2, the aqueous stream flowing through the stationary phase 23 in the column 24 is an aqueous carbonic acid solution. When the water contacts the anode 21 (and if the power source 20 is turned on), the water undergoes electrolysis, and hydronium ions are generated according to the following reaction:

Anode: $2H_2O \rightarrow 4H^+ + O_2(g) + 2e^-$

Similarly, when the water contacts the cathode 22, it undergoes electrolysis, and hydroxide ions are generated according to the following reaction:

Cathode: $2H_2O + 2e^- \rightarrow H_2(g) + 2OH^-$

Thus, hydronium ions are generated at the upstream end 41 of the column 24 and flow through the stationary phase 23 of column 24. The hydronium ions displace (i.e. exchange with and replace) the sodium ions on the stationary phase 23. The released sodium ions and excess hydronium ions generated at the upstream located anode 21 (along with the carbonic acid) flow to the downstream end 42 of the column 24 and contact the hydroxide ions generated at the downstream located cathode 22.

In the presence of the hydroxide ions, the carbonic acid and sodium ions react to form an eluant comprising sodium carbonate. (In addition, some of the sodium ions will react with the carbonic acid outside of the presence of the hydroxide ions). Furthermore, where the carbonic acid is present in excess compared to the sodium hydroxide (generated downstream), sodium bicarbonate will also be generated. Thus, a high purity eluant comprising carbonate ions is generated.

FIG. 3 illustrates another embodiment of the eluant generator of the present invention. Like parts in FIGS. 2 and 3 will be designated with like reference numbers. The column 24 is the same as that described with respect to FIG. 2. An additional column 25 that comprises a stationary phase 26 is provided.

Desirably, the stationary phase 26 comprises an anion exchange packing material with exchangeable carbonate ions although one skilled in the art will appreciate that other exchangeable anions may be used, depending on the application. Suitable anion exchange packing materials comprise particles of primary, secondary, tertiary, or quaternary amino functionalities, either organic or inorganic. Desirable anion exchange packing materials comprise quaternary amino functionality organic or inorganic particles.

The column 25 has an upstream end 43 and a downstream end 44. The upstream end 43 is located toward the column 24 relative to the downstream end 44. Conversely, the downstream end 44 is located away from the column 24 relative to the upstream end 43. The aqueous stream (coming from the column 24) flows through the stationary phase 26 of column 25 from the upstream end 43 towards the downstream end 44 of the column 25.

As illustrated in FIG. 3, the aqueous stream entering the column 24 contains deionized water (and does not contain carbonic acid as illustrated in FIG. 2). When the water contacts the anode 21 (and if the power source 20 is turned on), the water undergoes electrolysis, and hydronium ions are generated according to the following reaction:

Anode: $2H_2O \rightarrow 4H^+ + O_2(g) + 2e^-$

Similarly, when the water contacts the cathode 22, it undergoes electrolysis, and hydroxide ions are generated according to the following reaction:

Cathode: $2H_2O + 2e^- \rightarrow H_2(g) + 2OH^-$

Thus, hydronium ions are generated at the upstream end 41 of the column 24 and flow through the stationary phase 23 of column 24. The hydronium ions displace (i.e. exchange with and replace) the sodium ions on the stationary phase 23. The released sodium ions and excess hydronium ions generated at the upstream located anode 21 flow to the downstream end 42 of the column 24 and combine with the hydroxide ions generated at the downstream located cathode 22 to form sodium hydroxide and water respectively.

The aqueous stream from the column 24 (now containing sodium hydroxide) is then desirably flowed through a gas permeable tubing or membrane 135. The gas permeable tubing 135 is provided as discussed above with reference to the gas permeable tubing 132 of FIG. 1. By flowing the aqueous stream through the gas permeable tubing 135, electrolysis gases produced in the column 24 (oxygen and hydrogen gases) can be removed from the system. It is to be understood, however, that other types of tubing and other means for providing liquid communication between the columns 24 and 25 may be used.

The aqueous stream from the gas permeable tubing 135 is then flowed through the column 25. As the hydroxide ions (i.e. sodium hydroxide) are flowed through the column 25, they displace (i.e. exchange and replace) the carbonate ions on the stationary phase 26. The released carbonate ions then combine with the sodium ions in the aqueous stream to form an eluant comprising sodium carbonate and/or sodium bicarbonate. Thus, a high purity eluant comprising carbonate ions is generated.

Turning now to FIG. 4, another embodiment of the eluant generator of the present invention is illustrated. Like parts in FIGS. 2, 3, and 4 will be designated with like reference numbers. The eluant generator comprises a column 24 that is the same as that described with reference to FIG. 3. In addition, a column 37 is provided that is in parallel with the column 24 (in contrast to FIG. 3 where the two columns are in series).

The column 37 comprises a stationary phase 36. Desirably, the stationary phase 36 comprises an anion exchange packing material with exchangeable carbonate ions although one skilled in the art will appreciate that other exchangeable anions may be used, depending on the application. Suitable and preferable anion exchange packing materials are described above with reference to FIG. 3.

The column 37 further comprises electrodes 38 and 39 that are provided as discussed above with reference to the electrodes 21 and 22 in FIG. 2. Similarly, a power source 35 is provided as discussed above with reference to the power source 20 in FIG. 2. Alternatively, the same power source may supply power to electrodes 21, 22, 38, and 39. Preferably, the electrode 39 is a cathode located at the upstream end 45 of the column 37 and the electrode 38 is an anode located at the downstream end 46 of the column 37.

With reference to FIG. 4, an aqueous stream (containing deionized water) is flowed through both columns 24 and 37. When the water contacts the cathode 39 in the column 37 (and if the power source 35 is turned on), the water undergoes electrolysis, and hydroxide ions are generated according to the following reaction:

Cathode: $2H_2O + 2e^- \rightarrow H_2(g) + 2OH^-$

Similarly, when the water contacts the anode 38 of the column 37, it undergoes electrolysis, and hydronium ions are generated according to the following reaction:

Anode: $2H_2O \rightarrow 4H^+ + O_2(g) + 2e^-$

Thus, hydroxide ions are generated at the upstream end 45 of the column 37 and flow through the stationary phase 36 of column 37. The hydroxide ions displace (i.e. exchange with and replace) the carbonate ions on the stationary phase 36. The released carbonate ions and excess hydroxide ions generated at the upstream located cathode 39 flow to the downstream end 46 of the column 37 and combine with the hydronium ions generated at the downstream located anode 38 to form carbonic acid and water, respectively.

The aqueous stream from the column 37 (now containing carbonic acid) is then combined with the aqueous stream from the column 24 (which contains sodium hydroxide generated as described above with reference to FIG. 3) at a reaction sink 34. The reaction sink 34 can be any suitable device to ensure mixing of the sodium hydroxide and carbonic acid. For example, the reaction sink 34 may be a T-coupling. The sodium hydroxide and carbonic acid then react to form an eluant comprising sodium carbonate. In addition, where the carbonic acid is present in excess compared to the sodium hydroxide, sodium bicarbonate will also be generated. Thus, a high purity eluant comprising carbonate ions is generated.

As those skilled in the art will appreciate, in addition to generating a high purity eluant, the foregoing method can suitably be used in a method of gradient elution chromatography by controlling the amount of sodium hydroxide eluant generated in column 24 and/or the amount of carbonic acid generated in column 37. The higher the current in columns 24 and 37, the greater the concentration of sodium hydroxide and carbonic acid will respectively be generated. The concentration of the base or acid generated is directly proportional to the applied current and is inversely proportional to the aqueous stream (e.g. deionized water) flow rate. Thus, gradients are therefore possible through time-based current programming in the columns and may be generated in any of the embodiments shown in FIGS. 2-4 and variations of those embodiments.

The described method and apparatus for generating a high purity eluant has many advantages. For example, the eluant generation process is simplified and the labor involved in making the eluant is dramatically reduced. In addition, in several embodiments, only water flows through the pump rather than corrosive acids or bases that may destroy the pump seals and pistons. Moreover, in the generation of gradient eluants according to the present invention, only a single conventional pump is needed whereas, previously, a special pump that mixed and generated eluants of different concentrations was needed. Furthermore, because the eluant is not exposed to the atmosphere, the likelihood of contamination is reduced. With respect to the detection of sample ions, the use of the high purity eluant made according to the present invention reduces baseline shift, and provides better sensitivity, improved retention time stability, and increased peak resolution and integration.

While the described method and apparatus for the generation of the high purity eluant has been illustrated with reference to an ion chromatography system, it is to be understood that the invention may be used wherever a high purity eluant, such as an eluant comprising sodium carbonate, is desired. For example, it is applicable to liquid chromatography forms other than ion chromatography such as liquid chromatography using an ultraviolet detector. In addition, for example, a sodium carbonate solution made according to the present invention may be used in leather manufacture, particularly in chrome tannages, to control pH and, in the manufacture of paper, in the preparation of chemical pulps. It may also be used, for example, in the manufacture of glass, in the production of chemicals, in making soaps and detergents, in refining aluminum, in water softening, and in many other applications.

Furthermore, the method and apparatus of the present invention may also be used to generate a high purity reagent for chemical or other applications. For example, high purity sodium hydroxide may be generated to be used in the manufacture of other chemicals. In addition, for example, a high purity acid, such as hydrochloric acid, may be generated according to the present invention (by using a column with exchangeable chloride ions, flowing hydroxide ions through the column, which exchange with the chloride ions, and combining the chloride ions with hydronium ions) to be used in the manufacture of other chemicals. Accordingly, it is to be understood that, unless expressly stated otherwise or unless it is clear from the context, the term "eluant" as used herein and in the claims is not limited to an eluant for use in chromatography (e.g., it is also intended to mean a reagent for use in other applications).

It is therefore intended that the foregoing detailed description be regarded as illustrative rather than limiting, and that it be understood that it is the following claims, including all equivalents, that are intended to define the spirit and scope of this invention.

The invention claimed is:

1. A method for generating an eluant comprising:
   a. providing water;
   b. providing a first stationary phase comprising exchangeable cations;
   c. generating electrolysis ions by the electrolysis of water wherein the electrolysis ions are selected from the group consisting of hydronium ions and hydroxide ions;
   d. flowing the hydronium ions through the first stationary phase so that the hydronium ions replace the cations in the first stationary phase;
   e. combining the cations with the hydroxide ions to form a cation hydroxide solution before performing step (h);
   f. separating gases produced during the generation of electrolysis ions from the cation hydroxide solution after performing step (e);
   g. providing a source of carbonate ions consisting of a second stationary phase comprising carbonate ions; and
   h. flowing the cation hydroxide solution through the second stationary phase so that the hydroxide ions replace the carbonate ions and the cations combine with the carbonate ions to form an eluant containing carbonate ions.

2. The method of claim 1 wherein the cation is selected from the group consisting of sodium, potassium, and lithium.

3. A method for generating an eluant comprising:
   a. providing water;
   b. providing a first stationary phase comprising exchangeable cations;
   c. generating electrolysis ions by the electrolysis of water wherein the electrolysis ions are selected from the group consisting of hydronium ions and hydroxide ions;
   d. flowing the hydronium ions through the first stationary phase so that the hydronium ions replace the cations in the first stationary phase;
   e. combining the cations with the hydroxide ions to form a cation hydroxide solution before performing step (g);
   f. providing a source of carbonate ions consisting of aqueous carbonic acid, wherein the source of carbonate ions is provided by a method comprising providing a second stationary phase comprising carbonate ions; generating electrolysis ions by the electrolysis of water wherein the electrolysis ions are selected from the group consisting of hydronium ions and hydroxide ions; flowing the hydroxide ions through the second stationary phase so that the hydroxide ions replace the carbonate ions in the second stationary phase; and combining the carbonate ions with the hydronium ions; and g. combining the cations with carbonate ions to form an eluant containing carbonate ions.

4. The method of claim 3 wherein the cation is selected from the group consisting of sodium, potassium, and lithium.

5. A method for generating an eluant comprising:
a. providing water;
b. providing a first stationary phase comprising exchangeable cations;
c. generating electrolysis ions by the electrolysis of water wherein the electrolysis ions are selected from the group consisting of hydronium ions and hydroxide ions; and wherein the hydronium ions are exchangeable with the cations in the first stationary phase;
d. flowing the hydronium ions through the first stationary phase so that the hydronium ions replace the cations in the first stationary phase to form a cation hydroxide solution;
e. providing a second stationary phase comprising exchangeable carbonate ions; wherein the hydroxide ions are exchangeable with the carbonate ions in the second stationary phase; and
f. flowing the cation hydroxide solution through the second stationary phase so that the hydroxide ions replace the carbonate ions in the second stationary phase.

6. The method of claim 5 wherein the cation is selected from the group consisting of sodium, potassium, and lithium.

7. The method of claim 6 further comprising separating gases produced during the generation of electrolysis ions from the cation hydroxide solution after forming the cation hydroxide solution.

8. The method of claim 5 wherein the first and second stationary phases are provided in separate columns.

9. The method of claim 5 further comprising the steps of (g) providing sample ions and (h) separating the sample ions, wherein step (f) is performed before step (h).

10. A method for generating an eluant comprising:
a. providing water;
b. providing a first stationary phase comprising cations;
c. providing a second stationary phase comprising carbonate ions;
d. generating electrolysis ions in each of the first and second stationary phases by the electrolysis of water wherein the electrolysis ions are selected from the group consisting of hydronium ions and hydroxide ions, wherein the hydronium ions are exchangeable with the cations in the first stationary phase, and wherein the hydroxide ions are exchangeable with the carbonate ions in the second stationary phase;
e. flowing the hydronium ions generated in the first stationary phase through the first stationary phase so that the hydronium ions replace the cations in the first stationary phase;
f. combining the cations with hydroxide ions generated in the first stationary phase to form a cation hydroxide solution;
g. flowing the hydroxide ions generated in the second stationary phase through the second stationary phase so that the hydroxide ions replace the carbonate ions in the second stationary phase;
h. combining the carbonate ions with the hydronium ions generated in the second stationary phase to form a carbonic acid solution; and
i. combining the cation hydroxide solution with the carbonic acid solution.

11. The method of claim 10 wherein the cation is selected from the group consisting of sodium, potassium, and lithium.

12. The method of claim 10 wherein the first and second stationary phases are provided in separate columns.

13. The method of claim 10 further comprising the steps of (j) providing sample ions and (k) separating the sample ions, wherein step (i) is performed before step (k).

14. An apparatus for generating an eluant comprising:
a. a water reservoir;
b. a first stationary phase comprising cations and having an upstream portion and a downstream portion, and wherein the first stationary phase is in liquid communication with the water reservoir;
c. a second stationary phase comprising carbonate ions and having an upstream portion and a downstream portion, and wherein the second stationary phase is in liquid communication with the first stationary phase;
d. a first electrode in electrical communication with the upstream portion of the first stationary phase and a second electrode in electrical communication with the downstream portion of the first stationary phase;
e. a power supply for applying an electric potential between the first and second electrodes in electrical communication with the first stationary phase while an aqueous stream is flowing from the upstream portion to the downstream portion of the first stationary phase; and wherein the electric potential electrolytically generates hydronium and hydroxide ions.

15. The apparatus of claim 14 wherein the second stationary phase is in series with the first stationary phase.

16. The apparatus of claim 15 further comprising a gas permeable tubing in liquid communication between the first and second stationary phases.

17. The apparatus of claim 16 wherein the cation is selected from the group consisting of sodium, potassium, and lithium.

18. The apparatus of claim 14 wherein the second stationary phase is in parallel with the first stationary phase.

19. The apparatus of claim 18 further comprising a third electrode in electrical communication with the upstream portion of the second stationary phase and a fourth electrode in electrical communication with the downstream portion of the second stationary phase; and wherein the third and fourth electrodes are in electrical communication with the power supply so that an electric potential may be applied between the third and fourth electrodes.

20. The apparatus of claim 19 further comprising a reaction sink between, and in liquid communication with, the first and second stationary phases.

21. The apparatus of claim 20 wherein the cation is selected from the group consisting of sodium, potassium, and lithium.

22. The apparatus of claim 14 wherein the first stationary phase is contained in a first column and the second stationary phase is contained in a second column.

* * * * *